United States Patent
Robinson et al.

(10) Patent No.: US 10,350,374 B2
(45) Date of Patent: Jul. 16, 2019

(54) VENTILATOR SYSTEM AND METHOD

(71) Applicant: General Electric Company, Schenectady, NY (US)

(72) Inventors: Scott William Robinson, Bayside, WI (US); Paul Hunsicker, Hales Corners, WI (US)

(73) Assignee: General Electric Company, Schenectady, NY (US)

( * ) Notice: Subject to any disclaimer, the term of this patent is extended or adjusted under 35 U.S.C. 154(b) by 605 days.

(21) Appl. No.: 15/087,178

(22) Filed: Mar. 31, 2016

(65) Prior Publication Data

US 2016/0213867 A1    Jul. 28, 2016

Related U.S. Application Data

(63) Continuation of application No. 13/112,870, filed on May 20, 2011, now Pat. No. 9,326,736.

(51) Int. Cl.
*A61M 16/00* (2006.01)
*A61M 16/10* (2006.01)
(Continued)

(52) U.S. Cl.
CPC .......... *A61M 16/024* (2017.08); *A61B 5/091* (2013.01); *A61B 5/742* (2013.01);
(Continued)

(58) Field of Classification Search
CPC ............ A61M 16/0003; A61M 16/024; A61M 2230/46; A61M 2205/502; A61M 2016/0027; A61M 16/0051; A61B 5/742
See application file for complete search history.

(56) References Cited

U.S. PATENT DOCUMENTS 5,320,107 A * 6/1994 O'Brien ............... A61B 5/0871
600/538
6,556,902 B2 4/2003 Ing et al.
(Continued)

FOREIGN PATENT DOCUMENTS

CN    201346204 Y    11/2009
EP    1961378 A1    8/2008

OTHER PUBLICATIONS

The Acute Respiratory Distress Syndrome Network, Ventilation With Lower Tidal Volumes As Compared With Traditional Tidal Volumes For Acute Lung Injury and the Acute Respiratory Distress Syndrome, The New England Journal of Medicine, vol. 342, No. 18, May 4, 2000, pp. 1301-1308.

*Primary Examiner* — Colin W Stuart
*Assistant Examiner* — Douglas Y Sul
(74) *Attorney, Agent, or Firm* — Dean D. Small; The Small Patent Law Group, LLC

(57) ABSTRACT

A medical system having a ventilator coupled to a breathing circuit is provided. The ventilator is configured to exchange gases with the patient via the breathing circuit. The system includes one or more sensors configured to acquire measurement data associated with the patient, and a memory storing the measurement data. The system further includes a monitor configured to display a tidal volume and lung compliance viewer, and a processor. The processor is programmed to display a virtual gauge within the tidal volume and lung compliance viewer displayed on the monitor. The virtual gauge having a tidal volume indicator and a tidal volume and compliance indicator. The tidal volume and compliance indicator includes a color pattern positioned along a side of the tidal volume indicator. The color pattern representing a degree of tidal volume and compliance relationship with respect to a position on the virtual gauge.

20 Claims, 7 Drawing Sheets

(51) Int. Cl.
*A61B 5/00* (2006.01)
*A61B 5/091* (2006.01)
*A61M 16/01* (2006.01)

(52) U.S. Cl.
CPC .... *A61M 16/0003* (2014.02); *A61M 16/0051* (2013.01); *A61M 16/0057* (2013.01); *A61M 16/01* (2013.01); *A61M 2016/0015* (2013.01); *A61M 2016/0021* (2013.01); *A61M 2016/0027* (2013.01); *A61M 2016/0036* (2013.01); *A61M 2016/103* (2013.01); *A61M 2016/1025* (2013.01); *A61M 2016/1035* (2013.01); *A61M 2205/502* (2013.01); *A61M 2205/52* (2013.01); *A61M 2230/202* (2013.01); *A61M 2230/205* (2013.01); *A61M 2230/30* (2013.01); *A61M 2230/432* (2013.01); *A61M 2230/435* (2013.01); *A61M 2230/437* (2013.01); *A61M 2230/46* (2013.01)

(56) References Cited

U.S. PATENT DOCUMENTS

| | | | |
|---|---|---|---|
| 6,723,055 | B2 | 4/2004 | Hoffman |
| 6,860,266 | B2* | 3/2005 | Blike ..................... A61B 5/00 128/205.23 |
| 7,117,438 | B2 | 10/2006 | Wallace et al. |
| 7,334,578 | B2 | 2/2008 | Biondi et al. |
| 9,326,736 | B2* | 5/2016 | Robinson ............... A61B 5/091 |
| 2003/0156143 | A1 | 8/2003 | Westenskow et al. |
| 2007/0272242 | A1* | 11/2007 | Sanborn .................. A61B 5/08 128/204.23 |
| 2008/0146895 | A1* | 6/2008 | Olson ................ G08B 21/0453 600/301 |
| 2008/0202520 | A1 | 8/2008 | Mitton et al. |
| 2008/0202524 | A1 | 8/2008 | Mitton et al. |
| 2009/0113295 | A1* | 4/2009 | Halpern .............. A61B 5/14532 715/273 |
| 2009/0165798 | A1 | 7/2009 | Cong et al. |

\* cited by examiner

VENTILATOR SYSTEM AND METHOD

CROSS-REFERENCE TO RELATED APPLICATIONS

This application is a Continuation, and claims priority to and the benefit of the filing data of U.S. application Ser. No. 13/112,870, filed May 20, 2011, the subject matter of which is herein incorporated by reference in its entirety.

BACKGROUND OF THE INVENTION

The subject matter disclosed herein relates generally to respiratory care systems, and more particularly, to mandatory mechanical ventilation systems.

When patients are medically unable to breathe on their own, mechanical or forced ventilators can sustain life by providing requisite pulmonary gas exchanges for the patients. For example, conventional ventilators typically include electronic and pneumatic systems that control the pressure, flow rates, and/or volume of gases delivered to, and extracted from, patients needing medical respiratory assistance. Such control systems often include numerous user controls, such as knobs, dials, switches, and the like, for interfacing with treating clinicians, who support the patient's breathing by adjusting the pressure, flow rates, and/or volume of the patient's pulmonary gas exchanges, particularly as the condition and/or status of the patient changes. These parameter adjustments are challenging to control accurately, particularly using these conventional systems.

With respect to ventilation, this is a complex process of delivering oxygen to, and removing carbon dioxide from, alveoli within patients' lungs. Thus, conventional ventilators, particularly controlled mechanical ventilation (CMV) systems, include inputs that allow operating clinicians to select and use several modes of ventilation, either individually and/or in various combinations, using different ventilator setting controls. These mechanical ventilators have become increasingly sophisticated and complex, due in part to enhanced understandings of lung pathophysiology. Accordingly, many conventional ventilators are microprocessor-based and equipped with sensors that monitor patient pressure, flow rates, and/or volumes of gases, and then drive automated responses in response thereto. However, as these ventilators become more complicated and provide more options, the number and risk of potentially dangerous clinical decisions increases as well. Thus, clinicians often operate expensive, sophisticated machines, yet few follow clear, concise, and/or consistent guidelines for maximal use thereof. As a result, setting, monitoring, and interpreting ventilator parameters may be reduced to empirical judgment, resulting in less than optimal treatment.

Thus, the overall effectiveness of assisted ventilation ultimately depends on mechanical, technical, and physiological factors, with the clinician-ventilator-patient interface playing an important role. For example, clinicians often need to observe and control several factors to optimize the volume of air that is appropriate given the particular patient. However, it is often difficult for clinicians to observe and control these several factors at the same time.

BRIEF DESCRIPTION OF THE INVENTION

In one embodiment, a user interface for a medical system having a ventilator is provided. The user interface includes a memory storing one or more sensor measurements for a patient and a processor. The processor is programmed to display a visualization of a tidal volume determined from one of the sensor measurements of the patient and display a visualization of lung compliance for the patient, wherein the tidal volume visualization and the lung compliance visualization are displayed concurrently.

In another embodiment, a method for presenting ventilator data is provided. The method includes displaying a visualization of a tidal volume determined from one or more sensor measurements of a patient and concurrently displaying a visualization of lung compliance for the patient with the visualization of the tidal volume. The method also includes updating at least one of the tidal volume visualization or the lung compliance visualization based on a measured change corresponding to a received user input changing a ventilator setting for the patient.

In a further embodiment, a non-transitory computer readable storage medium for displaying ventilator information using a processor is provided. The non-transitory computer readable storage medium includes instructions to command the processor to display a visualization of a tidal volume determined from one or more sensor measurements of a patient and display a visualization of lung compliance for the patient, wherein the tidal volume visualization and the lung compliance visualization are displayed concurrently. The non-transitory computer readable storage medium also includes instructions to command the processor to update at least one of the tidal volume visualization or the lung compliance visualization based on a measured change corresponding to a received user input changing a ventilator setting for the patient.

DETAILED DESCRIPTION OF THE INVENTION

Figure 1:
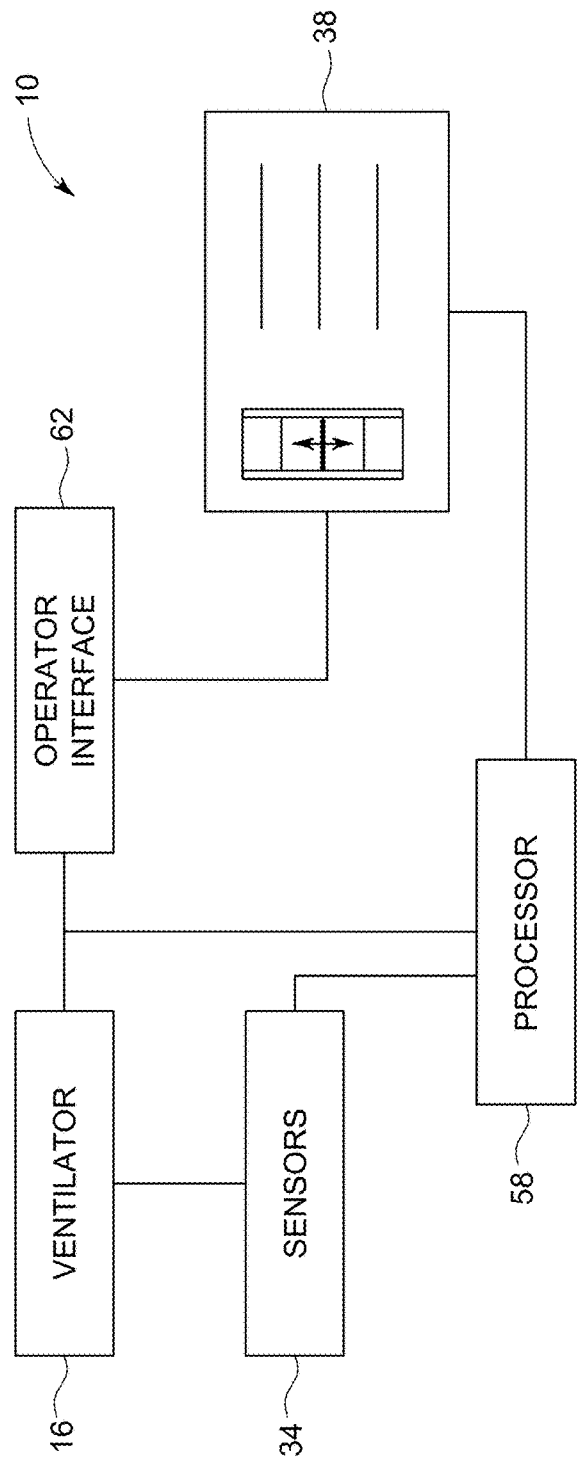
FIG. 1 is a simplified block diagram of a medical system in accordance with various embodiments.

The foregoing summary, as well as the following detailed description of certain embodiments, will be better understood when read in conjunction with the appended drawings. The figures illustrate diagrams of the functional blocks of various embodiments. The functional blocks are not necessarily indicative of the division between hardware circuitry. Thus, for example, one or more of the functional blocks (e.g., processors or memories) may be implemented in a single piece of hardware (e.g., a general purpose signal processor or a block or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

The various embodiments provide a user interface for a patient ventilator. In particular, various embodiments provide a Tidal Volume and Lung Compliance viewer (also referred to herein as a $V_T+C$ viewer) providing a user interface for a patient ventilator. Specifically, the viewer displays (e.g., superimposes) a visual representation of Tidal Volume ($V_T$=amount of air delivered) while presenting a visualization of Lung Compliance (C=measure the elasticity or stiffness of the lung). At least one technical effect of various embodiments is the ability to balance the contrasting settings that affect Tidal Volume and Lung Compliance using a single display.

The $V_T+C$ viewer may be implemented in a patient monitoring system providing mechanical ventilation. For example, the $V_T+C$ viewer may be implemented in a medical system 10 as illustrated in FIGS. 1 through 4. The medical system 10 in various embodiments provides for mechanically ventilating a patient 12 (shown in FIG. 2). With particular reference to FIG. 1, the medical system 10 also provides for visualization of the $V_T$ and C for use in controlling a ventilator 16 based on displayed compliance data in combination with measurement data from one or more sensors 34. The ventilator may be controlled via an operator interface 62 by a clinician viewing the visualized $V_T+C$ data, which is displayed concurrently on a monitor 38 to allow a user to view the balance between $V_T$ and C. A processor, for example, a processing subsystem 58 of the medical system 10 may process received measurements from the sensors 34 and other compliance information as described herein to update the monitor 38 with the $V_T+C$ data.

Figure 2:
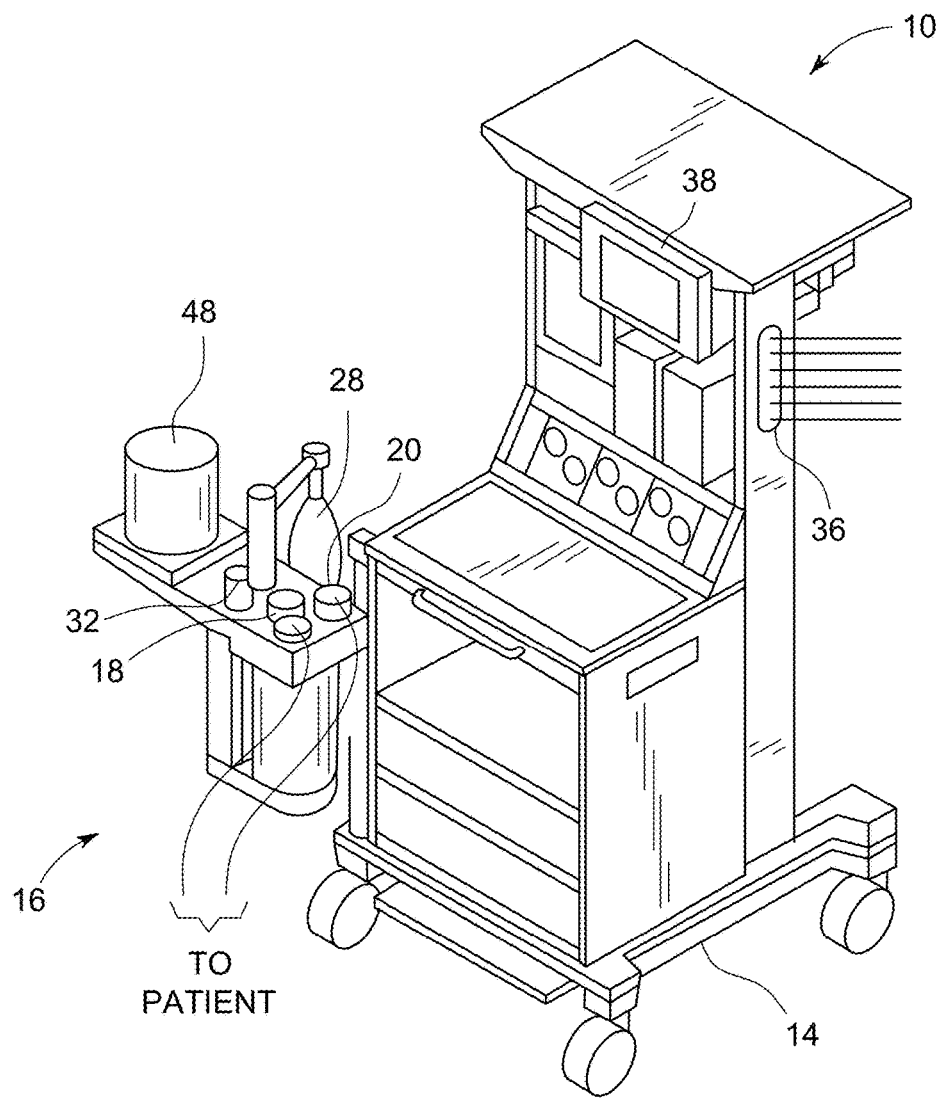
FIG. 2 is a front perspective view of the medical system of FIG. 1.
Figure 3:
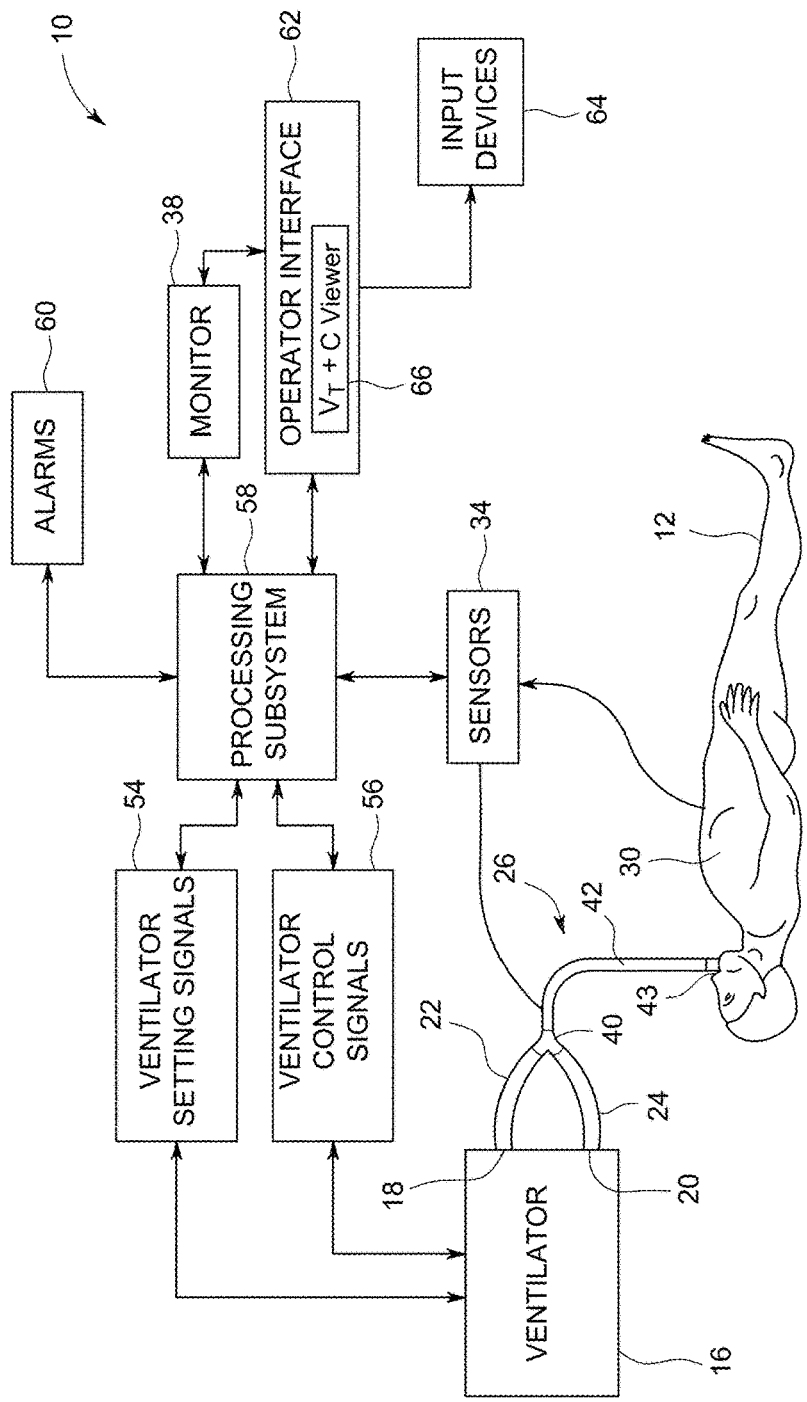
FIG. 3 is a detailed block diagram of the medical system of FIG. 1 providing ventilator support to a patient.
Figure 4:
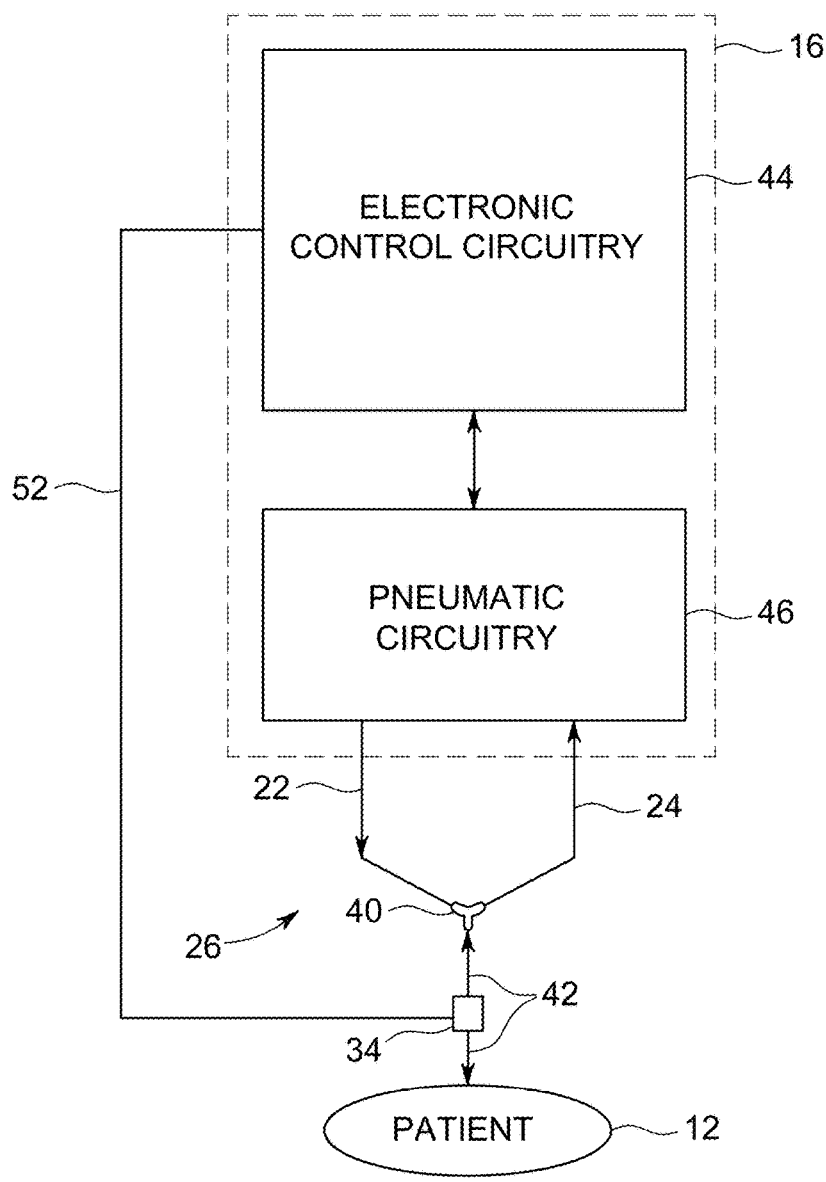
FIG. 4 is a block diagram of a ventilator of the medical system of FIG. 1.

With reference to one embodiment of the medical system 10, as shown in FIGS. 2 through 4, an anesthesia machine 14 includes the ventilator 16 having suitable connectors 18, 20 for connecting to an inspiratory branch 22 and expiratory branch 24 of a breathing circuit 26 leading to the patient 12. The ventilator 16 and breathing circuit 26 cooperate to provide breathing gases to the patient 12 via the inspiratory branch 22 and to receive gases expired by the patient 12 via the expiratory branch 24.

The ventilator 16 also optionally can be provided with a bag 28 for manually ventilating the patient 12. For example, the bag 28 can be filled with breathing gases and manually squeezed by a clinician (not shown) to provide appropriate breathing gases to the patient 12. Using this bag 28, or "bagging the patient," enables clinicians to manually and/or immediately control delivery of the breathing gases to the patient 12. The clinician can also sense conditions in the respiration and/or lungs 30 of the patient 12 according to the feel of the bag 28, and then accommodate for the same. The ventilator 16 can also provide a toggle 32 for switching and/or alternating between manual and automated ventilation when the bag 28 is provided.

The ventilator 16 further can receive inputs from the sensors 34 associated with the patient 12 (e.g., coupled to the patient 12) and/or the ventilator 16 at a processing terminal 36 for subsequent processing thereof, and which can be displayed on the monitor 38. Representative data received from the sensors 34 can include, for example, inspiratory time ($T_I$), expiratory time ($T_E$), natural exhalation time ($T_{EXH}$), respiratory rates (f), I:E ratios, positive end expiratory pressure (PEEP), fractional inspired oxygen ($F_IO_2$), fractional expired oxygen ($F_EO_2$), breathing gas flow (F), tidal volumes ($V_T$), temperatures (T), airway pressures ($P_{aw}$), arterial blood oxygen saturation levels ($S_aO_2$), blood pressure information (BP), pulse rates (PR), pulse oximetry levels ($S_pO_2$), exhaled $CO_2$ levels ($F_{ET}CO_2$), concentration of inspired inhalation anesthetic agent ($C_I$ agent), concentration of expired inhalation anesthetic agent ($C_E$ agent), arterial blood oxygen partial pressure ($P_aO_2$), arterial carbon dioxide partial pressure ($P_aCO_2$), and the like.

With particular reference now to FIG. 2, the ventilator 16 provides breathing gases to the patient 12 via the breathing circuit 26. Accordingly, the breathing circuit 26 typically includes the inspiratory branch 22 and expiratory branch 24. In one embodiment, one end of each of the inspiratory branch 22 and expiratory branch 24 is connected to the ventilator 16, while the other ends thereof are connected to a Y-connector 40, which can then connect to the patient 12 through a patient branch 42. An interface 43 also may be provided to secure the patient's 12 airways to the breathing circuit 26 and/or prevent gas leakage out thereof.

Referring now specifically to FIG. 3, the ventilator 16 can also include electronic control circuitry 44 and/or pneumatic circuitry 46. In particular, various pneumatic elements of the pneumatic circuitry 46 provide breathing gases to the lungs 30 of the patient 12 through the inspiratory branch 22 of the breathing circuit 26 during inhalation. Upon exhalation, the breathing gases are discharged from the lungs 30 of the patient 12 and into the expiratory branch 24 of the breathing circuit 26. This process can be iteratively enabled by the electronic control circuitry 44 and/or pneumatic circuitry 46 in the ventilator 16, which can establish various control parameters, such as the number of breaths per minute to administer to the patient 12, tidal volumes ($V_T$), maximum pressures, etc., that can characterize the mechanical ventilation that the ventilator 16 supplies to the patient 12. As such, the ventilator 16 may be microprocessor based and operable in conjunction with a suitable memory to control the pulmonary gas exchanges in the breathing circuit 26 connected to, and between, the patient 12 and the ventilator 16.

The various pneumatic elements of the pneumatic circuitry 46 may also include a source of pressurized gas (not shown), which can operate through a gas concentration subsystem (not shown) to provide the breathing gases to the lungs 30 of the patient 12. The pneumatic circuitry 46 may provide the breathing gases directly to the lungs 30 of the patient 12, as typical in a chronic and/or critical care application, or the pneumatic circuitry 46 may provide a driving gas to compress a bellows 48 (shown in FIG. 2) containing the breathing gases, which can, in turn, supply the breathing gases to the lungs 30 of the patient 12, as typical in an anesthesia application. In either case, the breathing gases iteratively pass from the inspiratory branch 22 to the Y-connector 40 and to the patient 12, and then back to the ventilator 16 via the Y-connector 40 and expiratory branch 24.

In the illustrated embodiment, one or more of the sensors 34, placed in the breathing circuit 26, can also provide feedback signals back to the electronic control circuitry 44 of the ventilator 16 via a feedback loop 52. More specifically, a signal in the feedback loop 52 may be proportional, for example, to gas flows and/or airway pressures in the patient branch 42 leading to the lungs 30 of the patient 12. Inhaled and exhaled gas concentrations (e.g., oxygen $O_2$, carbon dioxide $CO_2$, nitrous oxide $N_2O$, and inhalation anesthetic agents), flow rates (including, for example, spirometry), and gas pressurization levels, etc., may be captured by the sensors 34, as can the time periods between when the ventilator 16 permits the patient 12 to inhale and exhale, as well as when the patient's 12 natural inspiratory and expiratory flows cease.

Thus, the electronic control circuitry 44 of the ventilator 16 can also control displaying numerical and/or graphical information from the breathing circuit 26 on the monitor 38 of the medical system 10 (shown in FIG. 2), as well as other patient 12 and/or system 10 parameters from other sensors 34 and/or the processing terminal 36 (shown in FIG. 2). Additionally, visualizations of $V_T$ and C may be displayed as described in more detail herein. In other embodiments, various components can also be integrated and/or separated, as needed and/or desired.

The electronic control circuitry 44 can also coordinate and/or control, for example, other ventilator setting signals 54, ventilator control signals 56, and/or the processing subsystem 58, such as for receiving and processing signals from the sensors 34, display signals for the monitor 38 and/or the like, alarms 60, and/or the operator interface 62, which can include one or more input devices 64, etc., all as needed and/or desired and interconnected appropriately. The operator interface also includes a $V_T$ and C Viewer 66, which may be a module or other user control component or interface that enables the user to view and control the values of $V_T$ and C in relation to each other by display with a user interface tool on the monitor 38 as described herein.

The components are functionally depicted for illustration, wherein various components thereof can also be integrated and/or separated, as needed and/or desired. Other functional components, for example, one or more power supplies for the medical system 10 and/or anesthesia machine 14 and/or ventilator 16, etc. (not shown) may be provided.

Various embodiments provide a viewer, in particular a $V_T$+C viewer that is a user interface tool for the medical system 10, and specifically for controlling operation of the ventilator 16. For example, the $V_T$+C viewer enables a user, such as a clinician to balance and evaluate the contrasting settings that affect $V_T$ and C. Thus, the $V_T$+C viewer allows control of one more ventilator parameters or settings based on displayed information, which may be related in part to patient physiology. Accordingly, the various embodiments allow clinicians to control patient ventilation parameters throughout the respiratory cycle of the patient 12 and enables ventilation control or treatments to be individually controlled (e.g., optimized) for patients 12 subject to controlled mechanical ventilation (CMV).

As used herein $T_I$ is inspiratory time. More specifically, $T_I$ is the amount of time, measured in seconds, set on the ventilator 16 by the clinician, lasting from the beginning of the inspiration of the patient 12 to the beginning of the expiration of the patient 12.

The inspiratory times $T_I$ can be further broken down into a set inspiratory time $sT_I$, a delivered inspiratory time $dT_I$, and a measured inspiratory time $mT_I$. More specifically, the set inspiratory time $sT_I$ is the amount of time that the clinician sets on the ventilator 16 to deliver gases to the patient 12 during inspiration, while the delivered inspiratory time $dT_I$ is the amount of time that gases are actually allowed to be delivered to the patient 12 from the ventilator 16 during inspiration. Similarly, the measured inspiratory time $mT_I$ is the amount of time that the ventilator 16 measures for allowing gases to be delivered to the patient 12 during inspiration. Ideally, the set inspiratory time $sT_I$, delivered inspiratory time $dT_I$, and measured inspiratory time $mT_I$ are equal or substantially equal. However, if the clinician or ventilator 16 is searching for an optimal inspiratory time $T_{I-OPTIMAL}$, then each of these inspiratory times $T_I$ may be different or slightly different. For example, the clinician and/or ventilator 16 may have established a set of inspiratory time $sT_I$, yet the delivered inspiratory time $dT_I$ may deviate therefrom in the process of searching for, for example, the patient's 12 optimal inspiratory time $T_{I-OPTIMAL}$.

Further, $T_E$ as used herein is expiratory time, which is the amount of time, measured in seconds, set on the ventilator 16 by the clinician, lasting from the beginning of the patient's 12 expiration to the beginning of the patient's 12 inspiration. Accordingly, $T_E$ is the patient's 12 expiratory time. Like inspiratory times $T_I$, expiratory times $T_E$ can also be further broken down into a set expiratory time $sT_E$, a delivered expiratory time $dT_E$, and a measured expiratory time $mT_E$. More specifically, the set expiratory time $sT_E$ is the amount of time that the clinician sets on the ventilator 16 to allow the patient 12 to exhale gases during expiration, while the delivered expiratory time $dT_E$ is the amount of time that gases are allowed to be exhaled by the patient 12 during expiration. Similarly, the measured expiratory time $mT_E$ is the amount of time that the ventilator 16 measures for having allowed the patient 12 to exhale gases during expiration. Ideally, the set expiratory time $sT_E$, delivered expiratory time $dT_E$, and measured expiratory time $mT_E$ are equal or substantially equal. However, if the clinician or ventilator 16 is searching for an optimal expiratory time $T_E$, as described herein, then each of these expiratory times $T_E$ may be different or slightly different. For example, the clinician and/or ventilator 16 may have established a set expiratory time $sT_E$, yet the delivered expiratory time $dT_E$ may deviate therefrom in the process of searching, for example, for the patient's 12 natural exhalation time $T_E$.

I:E Ratios as used herein are the ratios Between $T_I$ and $T_E$. More specifically, I:E ratios measure inspiratory times divided by expiratory times, namely, $T_I/T_E$, which is commonly expressed as a ratio. Common I:E ratios are 1:2, meaning the patient 12 may inhale for a certain period of time (x) and then exhale for twice as long (2x). However, since some patients 12 may have obstructed pathologies (e.g., chronic obstructive pulmonary disease (COPD)) and/or slower exhalation, requiring the clinician to set longer expiratory times $T_E$, I:E ratios can also be set at ratios different ratios, for example, closer to 1:3 and/or 1:4, particularly to provide the necessary expiratory time $T_E$ for a given patient 12 to fully exhale. Although I:E ratios from 1:8 and 2:1 may be used, with common ventilators 16 providing 0.5 gradations therebetween.

Additionally, different parameters also may be measured. For example, $T_{EXH}$ as used herein is the natural exhalation time, which is the amount of time, measured in seconds, required for the patient's 12 natural exhalation flow to cease. Accordingly, $T_{EXH}$ is the patient's 12 natural exhalation time. Oftentimes, the patient's 12 expiratory time $T_E$ does not equal the patient's 12 natural exhalation time $T_{EXH}$, namely, the patient's 12 expiratory time $T_E$, as set by the clinician on the ventilator 16, often does not coincide with the patient's 12 natural exhalation time $T_{EXH}$. Moreover, in accordance with many default settings on many ventilators 16, respiratory rates f are commonly set between 6-10 breaths/minute and I:E ratios are commonly set at 1:2, resulting in many clinicians setting expiratory times $T_E$ between 4.0-6.6 seconds, as opposed to typical natural exhalation times $T_{EXH}$ being less than or equal to approximately 0.8-1.5 seconds. If the clinician or ventilator 16 sets the patient's 12 expiratory time $T_E$ less than or equal to the patient's 12 natural exhalation time $T_{EXH}$, there can be inadequate time for the patient 12 to expel the gases in the patient's 12 lungs 30. This can result in stacking breaths in the patient's 12 lungs 30 (i.e., so-called "breath stacking"), thereby inadvertently and/or unknowingly elevating the patient's 12 lung pressure.

As another example, the Positive End Expiratory Pressure (PEEP), which is the patient's 12 positive end expiratory pressure, may be measured, often measured in $cmH_2O$. Accordingly, PEEP is the amount of pressure in the patient's 12 lungs 30 at the end of the patient's 12 expiratory time $T_E$, as controlled by the ventilator 16. Like inspiratory times Ti and expiratory times $T_E$, positive end expiratory pressure PEEP can also be further broken down into a set positive end expiratory pressure sPEEP, a measured positive end expiratory pressure mPEEP, and a delivered positive end expiratory pressure dPEEP. More specifically, the set positive end expiratory pressure sPEEP is the amount of pressure that the clinician sets on the ventilator 16 for the patient 12, while the measured positive end expiratory pressure mPEEP is the amount of pressure in the patient's 12 lungs 30 at the end of the patient's 12 expiratory time $T_E$. Similarly, the delivered positive end expiratory pressure dPEEP is the amount of pressure delivered by the ventilator to the patient 12. Usually, the set positive end expiratory pressure sPEEP, measured positive end expiratory pressure mPEEP, and delivered positive end expiratory pressure dPEEP are equal or substantially equal. However, the measured positive end expiratory pressure mPEEP can be greater than the set positive end expiratory pressure sPEEP when breath stacking, for example, occurs.

As used herein, f is the respiratory rate. More specifically, f is the patient's 12 respiratory rate, measured in breaths/minute, set on the ventilator 16 by the clinician. Additionally, $V_T$, which is the Tidal Volume, defines the total volume of gases, measured in milliliters, delivered to the patient's 12 lungs 30 during inspiration. Accordingly, $V_T$ is the patient's 12 tidal volume. Like inspiratory times $T_I$ and expiratory times $T_E$, tidal volumes $V_T$ can also be further broken down into a set tidal volume $sV_T$, a delivered tidal volume $dV_T$, and a measured tidal volume $mV_T$. More specifically, the set tidal volume $sV_T$ is the volume of gases that the clinician sets on the ventilator 16 to deliver gases to the patient 12 during inspiration, while the delivered tidal volume $dV_T$ is the volume of gases actually delivered to the patient 12 from the ventilator 16 during inspiration. Similarly, the measured tidal volume $mV_T$ is the volume of gases that the ventilator 16 measures for having delivered gases to the patient 12 during inspiration. Ideally, the set tidal volume $sV_T$, delivered tidal volume $dV_T$, and measured tidal volume $mV_T$ are equal or substantially equal. However, if the clinician or ventilator 16 is searching for a set optimal tidal volume $sV_T$, as described herein, then each of these set tidal volumes $sV_T$ may be different or slightly different.

In operation, clinicians usually begin ventilation by selecting an initial set tidal volume $sV_T$, respiratory rate f, and I:E ratio. The respiratory rate f and I:E ratio usually determine the initial set inspiratory time $sT_I$ and initial set expiratory time $sT_E$ that the clinician sets on the ventilator 16. In other words, the actual set inspiratory time $sT_I$ and actual set expiratory time $sT_E$ that the clinician uses are usually determined in accordance with the following equations:

$$f = \frac{60}{sT_I + sT_E}$$

$$I{:}E = \frac{sT_I}{sT_E}$$

Moreover, the clinician usually makes these initial determinations based on generic rule-of-thumb settings, taking into account factors such as, for example, the patient's 12 age, weight, height, gender, geographical location, etc. Once the clinician makes these initial determinations, the $V_T$+C viewer may be used to adjust the settings of the ventilator 16 to balance $V_T$ and C. In particular, using the visualizations provided by various embodiments, the degree to which an ideal balance between $V_T$ and C has been achieved may be visually observed and determined, thereby allowing a user, such as a clinician to adjust the settings of the ventilator 16, such as to change the initial settings of $sV_T$, f, and I:E ratio.

Figure 5:
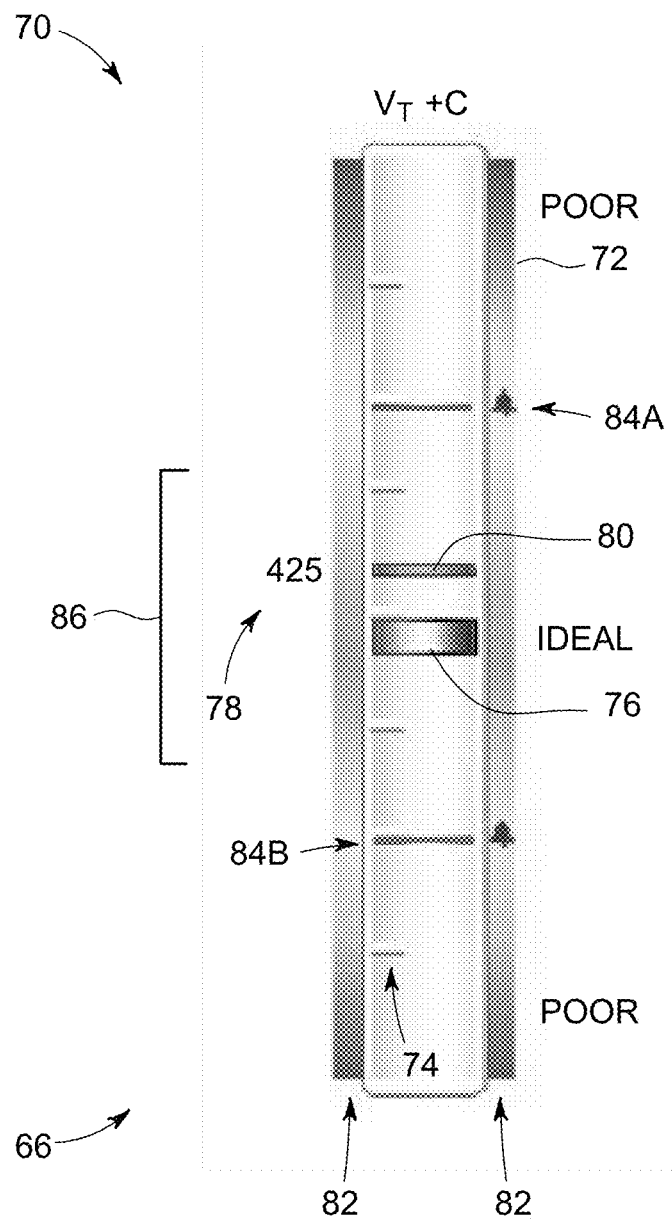
FIG. 5 illustrates ventilator information displayed in accordance with various embodiments.

In particular, in one embodiment as shown in FIG. 5, the $V_T$+C viewer 66 may be embodied as a user interface tool displayed on the monitor 38 (shown in FIGS. 1 and 2). The $V_T$+C viewer 66 may be a user interface tool that allow a user to view simultaneously or concurrently two different visualizations, namely visualizations of $V_T$ and C, which allows the user to then control the values of each in relation to each other. It should be noted that the $V_T$+C viewer 66 may be displayed on the monitor 38 with other information, such as typical data for use in controlling the ventilator 16 and for monitoring the patient 12.

Specifically, a graphical indicator portion 70, which is illustrated as $V_T$+C, is displayed and that provides visualizations of both $V_T$ and C at the same time. The graphical indicator portion 70 may take different forms, which in this embodiment is a virtual gauge 72 (or meter) that provides for the visual display or representation of both $V_T$ and C. However, other graphical indicators may be used, such as indicators having different scales, etc. In this embodiment, the gauge 72 is displayed as a virtual tube structure. The gauge 72 is dynamically updated to provide, in various embodiments, current or real-time $V_T$ and C information or data.

In the illustrated embodiments, the gauge 72 provides a visualization to allow correlation by a user of the $V_T$ and C information relative to each other, as well as optionally to other ventilator 16 information, such as f, the respiratory rate. More specifically, f is the patient's 12 respiratory rate and may also be visualized with an indication of the breaths for the patient 12. It should be noted that the various measurements providing ventilator measurement information may be performed by the one or more sensors 34 (shown in FIG. 2) and corresponding measurements data used by the $V_T$+C viewer 66.

The gauge 72 generally includes a scale portion 74 (e.g., scale marks or lines) that allows for the indication of data values that change during operation of the ventilator 16. In particular, a patient breath indicator 76 is provided that moves within the gauge 72 and along the scale portion 74 as the patient 12 breaths. Thus, the patient breath indicator 76 is a visualization of measured breaths of the patient 12. For example, the patient breath indicator 76 may be an indicator bar, such as a horizontal bar (or other visual indicator), that moves up and down (as viewed in FIG. 5) within the virtual tube structure as the patient 12 breathes. For example, the patient breath indicator 76 may move up as the ventilator 16 causes the patient 12 to breath in (based on measured inhalation time) and may move down as the patient breathes out (based on measured exhalation time). Accordingly, the patient breath indicator 76 moves up and down within the virtual tube structure of the gauge 72 to visualize and report to the user the breaths of the patient 12.

Additionally, a $V_T$ indicator 78 is provided to display a numerical value of the Tidal Volume (illustrated as 425). For example, the $V_T$ value may be displayed adjacent the scale portion 74. In one embodiment, a maximum breath indicator 80 is also displayed within the gauge 72, shown a horizontal bar within the virtual tube structure. The maximum breath indicator 80 indicates the maximum or top most point of the scale portion 74 reached during the last breath of the patient 12. It should be noted that the $V_T$ indicator 78 may move and be displayed adjacent the maximum breath indicator 80. Additionally, in various embodiments, the patient breath indicator 76 and the maximum breath indicator 80 are represented by different visually distinguishable elements or characteristics, such as by different bar thicknesses and/or colors.

In at least one embodiment, the value of the $V_T$ indicator 78 and position of the maximum breath indicator 80 within the virtual tube structure are updated with each breath of the patient 12. Thus, the measured data corresponding to the value of the $V_T$ indicator 78 and position of the maximum breath indicator 80 are for the last measured breath of the patient 12.

Additionally, a $V_T$ and Compliance indicator 82, which in one embodiment is a colored scale or pattern is provided along the gauge 72. In this embodiment, the $V_T$ and Compliance indicator 82 is a pattern or scale provided along both sides of the virtual tube structure. The $V_T$ and Compliance indicator 82 is a pattern or scale that indicates a degree of $V_T$ and Compliance relationship, such as from "Ideal" to "Poor". For example, the color scale of the $V_T$ and Compliance indicator 82 may range and fade from green to yellow to red as the scale moves from an Ideal relationship to a Poor relationship, which are indicated by text along the gauge 72. It should be noted that the Ideal level is generally in the middle of the gauge 72 and the Poor levels are at the ends of the gauge 72. However, the relative positions of these levels may be changed as desired or needed. Thus, the $V_T$ and Compliance indicator 82 provides a scale visualizing the degree of Lung Compliance C.

It should be note that the $V_T$ value may be determined using any suitable method and based on one or more measurements from the one or more sensors 34. Additionally, using any suitable method and based on one or more measurements from the one or more sensors 34, for example, pressure, flow and volume, the compliance for the patient 12 may be determined, and in particular extrapolated such that the range of coloring or the color pattern for the $V_T$ and Compliance indicator 82 may be displayed accordingly. For example, the color pattern and ranges for acceptable compliance levels may be based in part on data from other patients, which may have similar physical characteristic (e.g., weight, height, etc), other empirical data, model data, etc., and/or may be based on measurements of the patient 12. The information visualized by the $V_T$+C viewer 66 may be communicated and updated via the feedback loop 52 (shown in FIG. 4). Thus, the compliance indicator 82 may be embodied as a scale that visualizes a degree of lung compliance.

It should be noted that other indicators or markings may be provided, such as to show different conditions or provide warnings. For example, a $V_T$ threshold may be set, which may be determined based on a user input or predefined based on the scale of the compliance indicator 82, such as 40% of the range from Ideal to Poor. In particular, one or more warning indicators 84, which in this embodiment are colored vertical lines within the virtual tube structure and a warning icon, illustrated as a bell, may be displayed at the warning level. In the illustrated embodiment, the warning indicator 84a indicates an over inflation threshold and the warning indicator 84b indicates an under inflation threshold. Thus, if the patient breath indicator 76 moves above the warning indicator 84a, the lungs of the patient 12 are over inflated based on the determined compliance and the corresponding scale of the compliance indicator 82. Similarly, if the patient breath indicator 76 moves below the warning indicator 84b, the lungs of the patient 12 are under inflated based on the determined compliance and the corresponding scale of the compliance indicator 82. It should be noted that other visual or audible (e.g., sounds) warnings may be provided separately or in combination therewith.

Accordingly, in one embodiment, a user adjusts one or more settings of the ventilator 16 such that the $V_T$ stays within an Ideal region 86 (such as indicated by a green colored portion of the compliance indicator 82). Additionally, the adjustments are set in one embodiment to reduce or minimize the likelihood of the $V_T$ moving outside of the range of the warning indicators 84.

Figure 6:
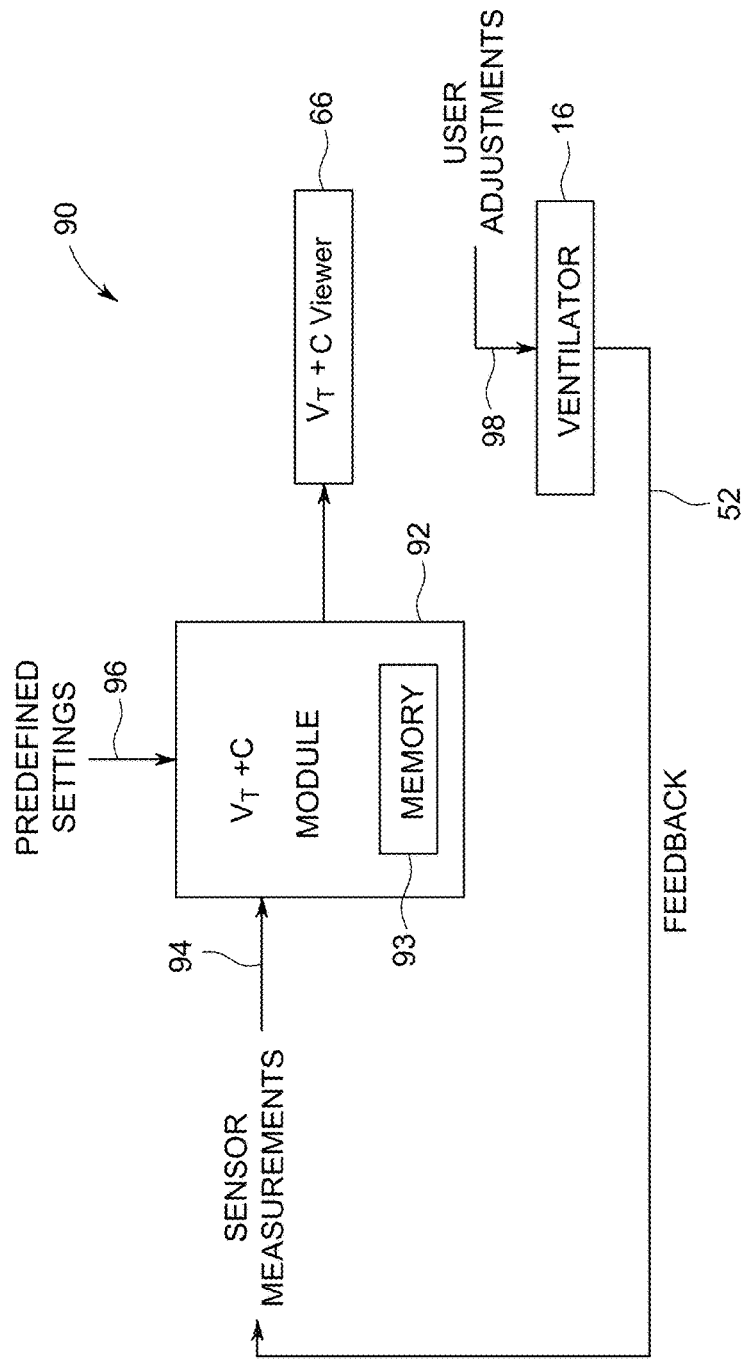
FIG. 6 is a block diagram of a visualization and compliance arrangement in accordance with various embodiments.

Thus, a visualization and compliance arrangement 90 as shown in FIG. 6 may be provided in accordance with various embodiments. The visualization and compliance arrangement 90 may be embodied as a user interface that allows a user to determine from an intuitive display the degree to which a balance has been achieve between the $V_T$ delivered by the ventilator 16 and the C for the patient 12. Accordingly, the user or clinician may be able to increase or optimize tidal volume in the context of lung compliance with the visualization and compliance arrangement 90.

In particular, the visualization and compliance arrangement 90 includes a $V_T$+C module 92 that may be implemented in software, hardware or a combination thereof, such as implemented as part of a processor (e.g., as part of the processing subsystem 58 shown in FIG. 3). The $V_T$+C module 92 is configured to implement various embodiments to display and visualize $V_T$+C information on the $V_T$+C viewer 66 as described in more detail herein. Specifically, the $V_T$+C module 92 receives as inputs sensor measurements 94, for example, from the sensors 34 (shown in FIG. 3) that are used by the $V_T$+C module 92, and which may be stored in a memory 93. The memory 93 may be provided in combination with the $V_T$+C module 92 or separate therefrom. In one embodiment, and for example, based on the sensor measurements 94 and predefined settings 96, the $V_T$+C module 92 determines a current patient breath cycle position and a maximum $V_T$ value for the last patient breath. Additionally, the $V_T$+C module 92 determines a scale for the compliance relationship ranging from Ideal to Poor as described in more detail herein. For example, historical population data or other known patient breath data may used by the $V_T$+C module 92 to determine the appropriate scale, as well as to set maximum and minimum threshold warning levels.

The determination and settings are displayed using the $V_T$+C viewer 66 as described in more detail herein, with one embodiment illustrated in FIG. 5. It should be noted that the data output from the $V_T$+C module 92 and used to update the $V_T$+C viewer 66 may be provided continuously, at predetermined time intervals, corresponding to predetermined events (e.g., after each breath), among others. The $V_T$+C module 92 provides updated information also based on user adjustments 98 to the ventilator 16, such as using the feedback loop 52, with sensor measurements 94 for the patient 12 corresponding to the adjusted settings provided to the $V_T$+C module 92. Thus, based on user adjusted settings of the ventilator 16, in at least one embodiment, real-time or near real-time lung compliance information is visualized in combination with tidal volume measurements.

Figure 7:
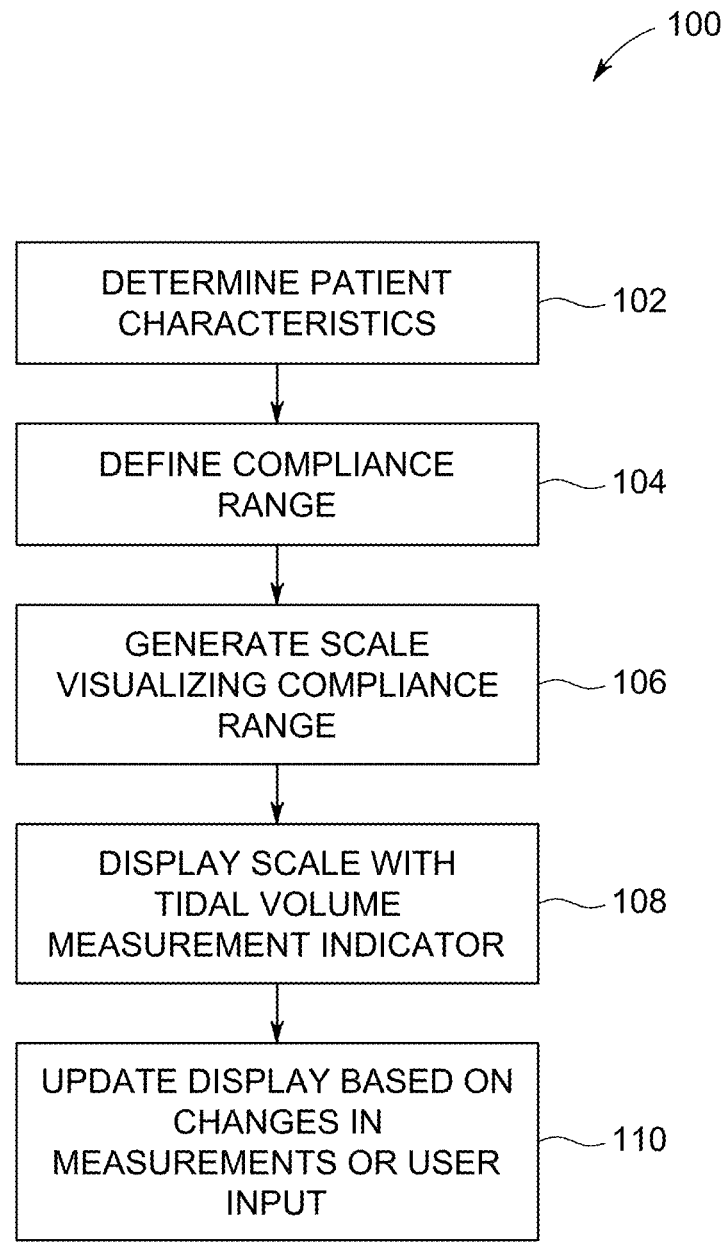
FIG. 7 is a flowchart of a method for visualizing ventilator measurement information in accordance with various embodiments.

Various embodiments also provide a method 100 as shown in FIG. 7 that visualizes ventilator measurement information for use in adjusting settings for the ventilator. The method 100 includes determining patient characteristics at 102. For example, patient specific information, such as the weight, height and age of the patient may be determined based on user entered information or previously stored data for the patient. Thereafter, a lung compliance range is determined for the patient at 104, such as based on the patient information and using population or standard data to determine an appropriate range for the patient. The compliance range may, for example, be extrapolated from the population or standard data, or from measured ventilator data for the patient, such as based on a measured pressure, flow and volume data of the lungs of the patient.

Thereafter, a scale is generated at 106 for visualizing the compliance range. For example, a color pattern for a compliance scale from Ideal to Poor compliance levels may be generated. In one embodiment, the compliance range may be generated such that the level of compliance indicated by changing color varies according to a predetermined formula (e.g., changes or fades colors every ⅓ of the range or over certain percentages of the range). The scale for the compliance range is then displayed at 108 along with other measurement information from the ventilator, for example, tidal volume measurement information (e.g., a tidal volume measurement indicator). Thus, in one embodiment, visualizations of lung compliance and tidal volume are displayed concurrently on a screen, which may be part of the $V_T$ C viewer 66.

The displayed information is updated at 110, for example, based on changes in patient conditions as measured by one or more sensors, which may result from user changes to the settings of the ventilator 16. The updated information may also be based on other user inputs. Additionally, the displayed visualizations may include indicators of thresholds and other similar markings. Also, the updating at 110 may be performed continuously, periodically, after certain events (e.g., after each patient breath), among others.

Thus, various embodiments provide for visualization of ventilator related information or data, such as the concurrent display of visualizations of tidal volume and lung compliance. The visualizations may be numerical, graphical or a combination thereof. Additionally, the various visualizations and displayed indicators may be modified as desired or needed, for example, based on user preferences or system settings.

Exemplary embodiments of a medical system with a ventilator are described above in detail. The components illustrated are not limited to the specific embodiments described herein, but rather, components of the system may be utilized independently and separately from other components described herein. For example, the medical system components described above may also be used in combination with other medical systems, such as medical imaging or diagnostic systems.

It should be noted that the various embodiments, for example, the modules described herein, may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive, optical disk drive, solid state disk drive (e.g., flash drive of flash RAM) and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A medical system comprising:
   a ventilator coupled to a breathing circuit, wherein the breathing circuit is adapted to be connected to a patient, the ventilator is configured to exchange gases with the patient via the breathing circuit;
   one or more sensors configured to acquire measurement data associated with the patient;
   a memory storing the measurement data;
   a monitor configured to display a tidal volume and lung compliance viewer; and
   a processor programmed to display a virtual gauge within the tidal volume and lung compliance viewer displayed on the monitor, the virtual gauge having a scale portion, a tidal volume indicator, and a tidal volume and compliance indicator, the tidal volume indicator displayed adjacent to the scale portion at a location relative to the scale portion that corresponds to a tidal volume, the tidal volume based on the measurement data, wherein the tidal volume and compliance indicator represents a degree of lung compliance and includes a color pattern positioned along a side of the scale portion, wherein a color of the color pattern varies along a length of the tidal volume and compliance indicator based on location relative to the scale portion, and
   wherein a relationship between the tidal volume and the lung compliance is indicated on the virtual gauge based on the location of the tidal volume indicator relative to the color pattern of the tidal volume and compliance indicator.

2. The medical system of claim 1, wherein the processor is further programmed to update the color pattern based on the measurement data.

3. The medical system of claim 1, wherein the color pattern is based on a second patient.

4. The medical system of claim 1, wherein a first position of the color pattern is indicative of a first degree of lung compliance and a second position of the color pattern is indicative of a second degree of lung compliance.

5. The medical system of claim 4, wherein the tidal volume indicator being displayed adjacent to the first position of the color pattern corresponds to an Ideal relationship between the tidal volume and the lung compliance, and the tidal volume indicator being displayed adjacent to the second position of the color pattern corresponds to a Poor relationship between the tidal volume and the lung compliance.

6. The medical system of claim 4, wherein the first position is associated with a first color of the color pattern, and the second position is associated with a second color of the color pattern.

7. The medical system of claim 1, wherein the processor is further programmed to update the color pattern in response to an adjustment in a setting of the ventilator or patient information.

8. The medical system of claim 1, wherein the processor is further programmed to determine a tidal volume threshold based on a scale of the tidal volume and compliance indicator.

9. The medical system of claim 8, wherein the processor is further programmed to display the tidal volume threshold within the virtual gauge at a predetermined location along the color pattern of the tidal volume and compliance indicator.

10. The medical system of claim 1, wherein the processor is further programmed to display a patient breath indicator traversing within the virtual gauge based on breaths of the patient.

11. The medical system of claim 1, wherein the processor is further programmed to display a maximum breath indicator on the scale portion of the virtual gauge, the maximum breath indicator displayed at a location along the scale portion corresponding to a maximum tidal volume for a previous patient breath.

12. The medical system of claim 1, wherein the color pattern of the tidal volume and compliance indicator has a first color at a middle section of the length of the tidal volume and compliance indicator and gradually ranges from the first color to a second color at each of two opposite end segments of the tidal volume and compliance indicator.

13. A method comprising:
    exchanging gases along a breathing circuit between a ventilator and a patient based on initial settings of the ventilator;
    acquiring measurement data from one or more sensors, wherein the measurement data is associated with the patient; and
    displaying a virtual gauge within the tidal volume and lung compliance viewer displayed on a monitor, the virtual gauge having a scale portion, a tidal volume indicator, and a tidal volume and compliance indicator, the tidal volume indicator displayed adjacent to the scale portion at a location relative to the scale portion that corresponds to a tidal volume, the tidal volume based on the measurement data, wherein the tidal volume and compliance indicator represents a degree of lung compliance and includes a color pattern positioned along a side of the scale portion, wherein a color of the color pattern varies along a length of the tidal volume and compliance indicator based on location relative to the scale portion, and
    wherein a relationship between the tidal volume and the lung compliance is indicated on the virtual gauge based on the location of the tidal volume indicator relative to the color pattern of the tidal volume and compliance indicator.

14. The method of claim 13, further comprising updating the color pattern based on a measured change corresponding to a received user input changing the initial settings of the ventilator.

15. The method of claim 13, further comprising determining a tidal volume threshold based on a scale of the tidal volume and compliance indicator.

16. The method of claim 13, further comprising displaying a patient breath indicator traversing within the virtual gauge based on breaths of the patient.

17. The method of claim 13, wherein the color pattern is based on a second patient.

18. The method of claim 13, wherein the displaying operation includes displaying the tidal volume indicator adjacent to the scale portion at a position that aligns within a middle segment of the length of the tidal volume and compliance indicator to indicate an Ideal relationship between the tidal volume and the lung compliance.

19. The method of claim 13, wherein the displaying operation includes displaying the tidal volume indicator adjacent to the scale portion at a position that aligns within an end segment of the length of the tidal volume and compliance indicator to indicate a Poor relationship between the tidal volume and the lung compliance.

20. A non-transitory computer readable storage medium of medical system using a processor, the non-transitory computer readable storage medium including instructions to command the processor to:

exchange gases along a breathing circuit between a ventilator and a patient based on initial settings of the ventilator;

acquire measurement data from one or more sensors, wherein the measurement data is associated with the patient; and display a virtual gauge within the tidal volume and lung compliance viewer displayed on a monitor, the virtual gauge having a scale portion, a tidal volume indicator, and a tidal volume and compliance indicator, the tidal volume indicator displayed adjacent to the scale portion at a location relative to the scale portion that corresponds to a tidal volume, the tidal volume based on the measurement data, wherein the tidal volume and compliance indicator represents a degree of lung compliance and includes a color pattern positioned along a side of the scale portion, wherein a color of the color pattern varies along a length of the tidal volume and compliance indicator based on location relative to the scale portion, and wherein a relationship between the tidal volume and the lung compliance is indicated on the virtual gauge based on the location of the tidal volume indicator relative to the color pattern of the tidal volume and compliance indicator.

* * * * *